US006710008B2

(12) United States Patent
Chang et al.

(10) Patent No.: US 6,710,008 B2
(45) Date of Patent: *Mar. 23, 2004

(54) METHOD OF MAKING MOLECULAR SIEVE CATALYST

(75) Inventors: Yun-Feng Chang, Houston, TX (US); Stephen N. Vaughn, Kingwood, TX (US); Jeffery W. Sprinkle, Baytown, TX (US); Fran A. Shipley, Crosby, TX (US); Kenneth R. Clem, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/052,058

(22) Filed: Jan. 17, 2002

(65) Prior Publication Data

US 2003/0135079 A1 Jul. 17, 2003

(51) Int. Cl.[7] ............... B01J 27/182; B01J 29/82; B01J 29/04
(52) U.S. Cl. ............... 502/214; 502/60; 502/63; 502/64; 502/68
(58) Field of Search ............... 502/60, 63, 64, 502/68, 214

(56) References Cited

U.S. PATENT DOCUMENTS

| | | | |
|---|---|---|---|
| 3,816,342 A | 6/1974 | Plank et al. | |
| 4,946,814 A | 8/1990 | Shi et al. | 502/62 |
| 5,998,329 A | 12/1999 | Derolf et al. | 502/407 |
| 6,153,552 A | 11/2000 | Wachter et al. | 502/208 |
| 6,509,290 B1 * | 1/2003 | Vaughn et al. | 502/214 |

FOREIGN PATENT DOCUMENTS

| | | | |
|---|---|---|---|
| EP | 0 359 841 | 3/1990 | C10G/3/00 |
| EP | 0 359 843 | 3/1990 | C10G/3/00 |
| WO | WO 99/21651 | 5/1999 | B01J/29/04 |
| WO | WO 02/05950 | 1/2002 | B01J/29/00 |
| WO | WO 02/070132 | 9/2002 | B01J/35/00 |

* cited by examiner

Primary Examiner—Elizabeth D. Wood

(57) ABSTRACT

Disclosed is a method for making molecular sieve catalyst particles. Dried molecular sieve catalyst particles are used to make the catalyst. The dried molecular sieve catalyst particles are put into an aqueous solution and stirred to make a slurry. The slurry is dried to make the molecular sieve catalyst particles. Optionally, the dried molecular sieve catalyst particles made from the slurry are calcined.

62 Claims, No Drawings

METHOD OF MAKING MOLECULAR SIEVE CATALYST

FIELD OF THE INVENTION

This invention relates to a method of making molecular sieve catalyst. In particular, this invention relates to a method of making molecular sieve catalyst from dried molecular sieve catalyst particles.

BACKGROUND OF THE INVENTION

A molecular sieve is generally a microporous structure composed of either crystalline aluminosilicate, belonging to a class of materials known as zeolites, or crystalline aluminophosphates, or crystalline silicoaluminophosphates. Molecular sieves can be made by hydrothermal crystallization from a reaction mixture comprising reactive sources of silicon and/or aluminum and/or phosphorous containing compounds, usually in the presence of one or several organic amine or quaternary ammonium salt as structure directing agent, also known as template.

Molecular sieve catalysts are compositions made of molecular sieve particles bound together to form particles larger than the molecular sieve components. The molecular sieve catalyst particles can also include other components such as binders, fillers, like clay, and optionally other catalytically active agents such as rare earth metal oxides, transition metal oxides, or noble metal components.

Conventional methods of making molecular sieve catalyst particles include mixing together molecular sieve and binder, as well as other optional components such as fillers and other catalytic components. The mixture is typically stirred in solution to form a slurry, and the slurry is dried to form molecular sieve catalyst particles. Following drying, the particles are calcined to harden, as well as activate, the catalyst particles.

For example, WO 99/21651 describes a method for making molecular sieve catalyst. The method includes the steps of mixing together a molecular sieve and an alumina sol, the alumina sol being made in solution and maintained at a pH of 2 to 10. The mixture is then spray dried and calcined. The calcined product is reported to be relatively hard, i.e., attrition resistant.

U.S. Pat. No. 6,153,552 describes another method for making molecular sieve catalyst. The catalyst is made by mixing together a silicon containing oxide sol as a binder material and a molecular sieve material. The pH of the mixture is adjusted prior to spray drying. Following spray drying, the catalyst material is calcined to form a finished catalyst product, which is reported to be relatively hard, i.e., attrition resistant.

During the manufacture of molecular sieve catalyst, catalyst particles can be made which have undesirable properties such as undesirable attrition resistance properties or undesirable particle size properties. Rather than discarding such catalyst particles, it would be beneficial to find a method that allows for the catalyst particles to be remanufactured or recycled so as to provide properties which are acceptable to the user or manufacturer.

SUMMARY OF THE INVENTION

This invention provides a method for making molecular sieve catalyst particles from catalyst particles which have certain undesirable properties. In essence, this invention provides for the remanufacturing or recycling or re-working of molecular sieve catalyst to provide properties which are acceptable to the user or manufacturer.

In one embodiment, there is provided a method of making molecular sieve catalyst particles, comprising
  a) providing a first dried molecular sieve catalyst;
  b) combining the first dried molecular sieve catalyst with water to form a water-catalyst composition;
  c) mixing the water-catalyst composition to form a slurry; and
  d) drying the slurry to form particles of a second dried molecular sieve catalyst.

In another embodiment, there is provided a method of recycling molecular sieve catalyst particles having undesired properties, comprising
  (i) mixing a composition comprising molecular sieve, binder and water;
  (ii) drying the composition to form a first dried molecular sieve catalyst;
  (iii) combining at least a portion of the first dried molecular sieve catalyst with water to form a water-catalyst composition;
  (iv) mixing the water-catalyst composition to form a slurry;
  (v) drying the slurry to form particles of a second dried molecular sieve catalyst.

In yet another embodiment, there is provided a method of making a molecular sieve catalyst composition, comprising: providing first dried molecular sieve catalyst particles, wherein the first dried molecular sieve catalyst particles yield, upon calcining, a calcined molecular sieve composition having greater than 5 wt % catalyst particles having an average particle diameter greater than or equal to 250 microns; combining the dried molecular sieve catalyst particles with water to form a slurry; and drying the slurry to form the molecular sieve catalyst composition.

In all embodiments of the invention, it is preferred that the water combined with the first dried molecular sieve catalyst comprises at least 95 wt % water and/or is substantially free of any molecular sieve particle. Preferably, the water is at a substantially neutral pH prior to combining with the dried molecular sieve catalyst particles.

The first dried molecular sieve catalyst may be uncalcined and may thus contain template material. Preferably, the template material is selected from the group consisting of triethylamine, cyclohexylamine, piperidine, dipropylamine, pyridine, isopropylamine, tetraethyl ammonium salts, and mixtures thereof.

It is preferred that the first dried molecular sieve catalyst and water be mixed so to break apart the particles of the first dried molecular sieve catalyst.

A slurry is formed, preferably having a viscosity of from 100 cP to 9,000 cP measured using a Brookfield LV-DVE viscometer with a No. 3 spindle at 10 rpm, and a solids content of from 10 wt % to 75 wt %.

The slurry is then dried to form particles of a second dried molecular sieve catalyst. Preferably drying is by spray drying.

The particles of the second dried molecular sieve catalyst may be submitted to calcination. Preferably, the molecular sieve catalyst particles obtained in e) have an EMARI of not greater than 1 wt %/hr, preferably not greater than 0.7 wt %/hr, most preferably not greater than 0.3 wt %/hr, and/or have a particle size such that 50% of the particles have a diameter larger than 30 μm and smaller than 150 μm.

The first dried molecular sieve catalyst preferably comprises a silicoaluminophosphate molecular sieve, more preferably selected from the group consisting of SAPO-18, SAPO-34, SAPO-35, SAPO-44, SAPO-56, ALPO-18 and ALPO-34, metal containing molecular sieves thereof, and mixtures thereof, even more preferably selected from the group consisting of SAPO-18, SAPO-34, ALPO-34 and ALPO-18, metal containing molecular sieves thereof, and mixtures thereof. In another embodiment, the first dried molecular sieve catalyst is selected from the group consisting of silicoaluminphosphate molecular sieves having CHA, AEI or a combination of CHA and AEI framework type.

The first dried molecular sieve catalyst may also comprise a binder selected from the group consisting of hydrated alumina, silicas, and/or other inorganic oxide sol and/or a filler selected from the group consisting of clays, clay-type compositions and mixtures thereof.

The present invention also relates to a calcined molecular sieve catalyst composition comprising catalyst particles, wherein the catalyst particles, after being submitted to calcination, have an EMARI of equal or less than 0.7 wt %/hr, preferably less than 0.3 wt %/hr.

The molecular sieve catalysts prepared by the method of the present invention are useful catalysts for the conversion of feedstocks comprising at least one oxygenate into olefins.

DETAILED DESCRIPTION OF THE INVENTION

This invention provides a method for making molecular sieve catalyst particles. The method is accomplished by combining a first dried molecular sieve catalyst with water to make a water-catalyst composition, making a slurry from the water-catalyst composition, and drying the slurry to produce a second dried molecular sieve catalyst. The method particularly provides for the re-manufacturing, recycling or re-working of dried or substantially dried, or partially dried molecular sieve catalysts to yield catalyst particles with properties that are acceptable to the user or manufacturer. Such properties are usually observed after the dried molecular sieve catalyst is calcined. These properties include acceptable particle size, particle size distribution, particle density, and particle hardness.

According to the invention, the first dried molecular sieve catalyst is combined with water to form a water-catalyst composition. The water with which the first dried molecular sieve is combined is essentially pure water, that is, water comprising at least 95 wt % water, preferably at least 97 wt % water, more preferably at least 98 wt % water. The water may optionally contain less than 5 wt %, preferably less than 3 wt %, and more preferably less than 2 wt %, other compounds. Non-limiting examples of such compounds include alcohols, aldehydes, esters, ethers, salts, soluble carbonates, oxides, hydroxides, acids, bases, water soluble polymers. Preferably, though, the water should contain as little as possible of such additional components. In any event, water with which the first dried molecular sieve composition is combined is essentially free of any molecular sieve particle, i.e. the water contains less than 1 wt % molecular sieve.

In combining the first dried molecular sieve catalysts with water, the order of addition is not critical. The first dried molecular sieve catalyst may be added to water, water may be added to the first dried molecular sieve catalyst or water and the first dried molecular sieve catalyst may be combined simultaneously.

The water-catalyst composition contains particles of the first dried molecular sieve catalyst and water. Optionally, other components may be added to the water-catalyst composition. However, the water-catalyst composition contains no other molecular sieve than that originally present in the first dried molecular sieve catalyst. The process of the present invention thus differs from other catalyst recycling processes in which the recycled molecular sieve catalyst particles are mixed with a slurry containing additional molecular sieve. In such processes, the water-catalyst composition formed during the recycling process contains additional molecular sieve, i.e. molecular sieve that was not originally present in the recycled catalyst particles.

The first dried molecular sieve catalyst is made of catalyst particles which contain molecular sieve particles bound together to form catalyst particles larger than the individual molecular sieve particles. The molecular sieve catalyst particles can also include other components such as fillers, like clay, and other catalytically active agents, for example, metal compounds.

The first dried molecular sieve catalyst has properties that make it unsuitable for its intended use. The present invention provides a method allowing to recycle, or re-work such undesired molecular sieve catalyst to produce new molecular sieve catalyst having the desired properties.

For purposes of this invention, dried means that the mixture used to form the molecular sieve catalyst has been submitted to heat in a drying or forming unit but has not been calcined. Dried also means that at least a portion of the liquid used during the manufacture, also referred to as formulation, of the catalyst has been removed. The method of the invention can be used with molecular sieve catalyst compositions from which the liquid used for manufacture has been partially, substantially or totally removed.

After such drying, the molecular sieve may still contain structure directing molecules (templates) used during the preparation of the molecular sieve. As used in the present description, drying does not include calcination. Calcination is essentially a combustion process that takes place at a higher temperature than that of a drying process. The calcination process takes place preferably in the presence of an oxygen-containing gas at a temperature from about 200° C. to about 900° C., preferably from about 250° C. to about 850° C., and more preferably from about 300° C. to about 800° C.

In order to determine whether a dried molecular sieve catalyst has acceptable or unacceptable properties, it is usually necessary to calcine a portion of the molecular sieve catalyst to determine one or more properties. If the portion of calcined catalyst demonstrates one or more undesirable properties, the dried, but uncalcined, remaining portion of the catalyst is combined with water to form a water-catalyst composition. The water-catalyst composition is mixed to from a slurry. The slurry is then dried to form the so-called second catalyst particles. A sample of this material can then be calcined and re-tested for the desired properties. If the desired properties are achieved, then the remainder of the second dried catalyst may be calcined, if desired. If one or more properties are still not achieved, the process steps are repeated until satisfactory testing results are achieved, and the remainder of dried catalyst can then be calcined, if desired. The invention is thus extremely useful to monitor and optimize catalyst manufacturing processes.

In an embodiment of the invention, the first dried molecular sieve catalyst contains template material. Template materials, often also called structure directing agents, are chemical compounds which are used to make the crystalline molecular sieves. During the formation of the molecular sieves, a crystalline structure is formed which essentially wraps around the template material.

The template may still be present in the first dried catalyst composition. It will eventually be removed from the second dried catalyst composition to form a final catalyst composition product. The template is typically removed by calcination or other chemical process such as an elution type process, which leaves behind a vast pore system within the crystalline structure. The pore system is generally referred to as an intracrystalline pore system.

Representative templates which can be included in the first dried catalyst particles include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate.

The first dried molecular sieve catalyst used to make the catalysts of this invention can include any of a variety of molecular sieve components. The components include zeolites or non-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from 3.5 to 4.2 angstroms. These pore sizes are typical of molecular sieves having 8 membered rings.

Conventional crystalline aluminosilicate zeolites having catalytic activity are desirable molecular sieves that can be used in making the catalyst of this invention. Examples of such zeolite materials are described in U.S. Pat. Nos. 3,660, 274 and 3,944,482, both of which are incorporated herein by reference. Non-limiting examples of zeolites which can be employed in the practice of this invention, include both natural and synthetic zeolites. These zeolites include zeolites of the structural types included in the "Atlas of Zeolite Framework Types" edited by Ch. Baerlocher, W. M. Meier, D. H. Olson, Fifth Revised edition, Elsevier, Amsterdam, 2001, he descriptions of which are incorporated herein by reference.

Zeolites typically have silica-to-alumina ($SiO_2/Al_2O_3$) mole ratios of at least about 2, and have uniform pore diameters from about 3 to 15 Angstroms. They also generally contain alkali metal cations, such as sodium and/or potassium and/or alkaline earth metal cations, such as magnesium and/or calcium. In order to increase the catalytic activity of the zeolite, it may be desirable to decrease the alkali metal content of the crystalline zeolite to less than about 5 wt. %, preferably less than about 1 wt. %, and more preferably less than about 0.5 wt. %. The alkali metal content reduction, as is known in the art, may be conducted by exchange with one or more cations selected from the Groups IIB through VIII of the Periodic Table of Elements (the Periodic Table of Elements referred to herein is given in Handbook of Chemistry and Physics, published by the Chemical Rubber Publishing Company, Cleveland, Ohio, 45th Edition, 1964 or 73rd Edition, 1992), as well as with hydronium ions or basic adducts of hydronium ions, e.g., $NH_4^+$, capable of conversion to a hydrogen cation upon calcination. Desired cations include rare earth cations, calcium, magnesium, hydrogen and mixtures thereof. Ion-exchange methods are well known in the art and are described, for example, in U.S. Pat. Nos. 3,140,249; 3,142, 251 and 1,423,353, the teachings of which are hereby incorporated by reference.

Examples of zeolites suitable for use in this invention include large pore zeolites, medium pore zeolites, and small pore zeolites. A large pore zeolite generally has a pore size of >7 Å and includes zeolite types such as MAZ, MEI, FAU, EMT. Examples of large pore zeolites include zeolite L, zeolite Y, zeolite X, offretite, omega, Beta, mordenite, ZSM-3, ZSM-4, ZSM-18, and ZSM-20. A medium pore size catalyst generally has a pore size <7 Å, preferably from about 5 Å to about 6.8 Å; and generally the pore apertures consist of about 10 to 12, preferably about 10, membered ring structures and include MFI, MEL, MTW, EUO, MTT, HEU, FER, and TON. Examples of medium pore zeolite include ZSM-34, ZSM-38, and ZSM-48. A small pore size zeolite has a pore size from about 3 Å to about 5.0 Å. Generally, the pore apertures of the structure consist of from about 8 to 10, preferably about 8, membered ring structures and include CHA, ERI, KFI, LEV, and LTA. Examples of small pore zeolite include ZK-4, ZK-5, zeolite A, zeolite T, gmelinite, chinoptilolite, chabasite and erionite. The zeolites can also comprise gallosilicates and titanosilicates.

Non-zeolite molecular sieves can also be included in the first dried molecular sieve catalyst particles used to make the catalysts of this invention. Preferred non-zeolite molecular sieves include metalloaluminophosphate molecular sieves.

The metalloaluminophosphate molecular sieve may be represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Si, Ge, Co, Cr, Cu, Fe, Ga, Ge, Mg, Mn, Ni, Sn, Ti, Zn, Zr and mixtures thereof. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Examples of metalloaluminophosphate molecular sieves which may be present in the first dried molecular sieve catalysts have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851, 106 (CrAPO), U.S. Pat. Nos. 4,758,419, 4,882,038, 5,434, 326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [$QO_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other metalloaluminophosphate molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001(thorium containing molecular sieve), and R. Szostak, *Handbook of Molecular Sieves*, Van Nostrand Reinhold, New York, N.Y. (1992), which are all herein fully incorporated by reference.

Most preferably, the molecular sieves present in the first dried molecular sieve catalyst are silicoaluminophosphate (SAPO) molecular sieves, aluminophosphate molecular sieves and metal substituted forms thereof.

Non-limiting examples of SAPO and ALPO molecular sieves that may be present in the first dried molecular sieve catalyst of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

As used herein, the term mixture is synonymous with combination and is considered a composition of matter having two or more components in varying proportions, regardless of their physical state. In particular, it encompasses physical mixtures as well as intergrowths of at least two different molecular sieve structures, such as for example those described in PCT Publication No. WO 98/15496. In an embodiment, the molecular sieve is an intergrowth material having two or more distinct phases of crystalline structures within one molecular sieve composition. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type. In a further embodiment the molecular sieve comprises a mixture of intergrown material and non-intergrown material.

The first dried molecular sieve catalyst compositions may also contain binder. Non-limiting examples of binders that may be present alone or in combination include various types of hydrated aluminas, silicas, and/or other inorganic oxide sols. One preferred alumina containing sol is aluminium chlorohydrate. The inorganic oxide sol acts like glue binding the molecular sieve and other materials that may also be present in the catalyst composition such as a matrix or filler together, particularly after thermal treatment. Upon heating, the inorganic oxide sol, is converted into an inorganic oxide matrix component. For example, an alumina sol will convert to an aluminium oxide matrix following heat treatment.

Aluminium chlorohydrate, a hydroxylated aluminium based sol containing a chloride counter ion also known as aluminium chlorohydrol, has the general formula $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105–144, Elsevier, Amsterdam, 1993, which is herein incorporated by reference. In another embodiment, one or more binders are present in combination with one or more other non-limiting examples of alumina materials such as aluminium oxyhydroxide, γ-alumina, boehmite and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including some silicon. In yet another embodiment, the binders are peptised alumina made by treating alumina hydrates such as pseudobohemite, with an acid, preferably an acid that does not contain a halogen, to prepare sols or aluminium ion solutions. Non-limiting examples of commercially available colloidal alumina sols include Nalco 8676 available from Nalco Chemical Co., Naperville, Ill., and Nyacol available from the Nyacol Nano Technology Inc., Boston, Mass.

The first dried molecular sieve may also comprise one or more matrix or filler material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include kaolins known as, for example, Dixie, McNamee, Georgia and Florida clays. Non-limiting examples of other matrix materials include: halloysite, kaolinite, dickite, nacrite, or anauxite. In one embodiment, the matrix material, preferably any of the clays, are subjected to well known modification processes such as calcination and/or acid treatment and/or chemical treatment before being used in catalyst formulation processes.

In one preferred embodiment, the matrix material is a clay or a clay-type composition, preferably a clay or clay-type composition having a low iron or titania content, and most preferably the matrix material is kaolin. Kaolin has been found to form a pumpable, high solid content slurry; it has a low fresh surface area, and it packs together easily due to its platelet structure. A preferred average particle size of the matrix material, most preferably kaolin, is from about 0.1 μm to about 0.6 μm with a $d_{90}$ particle size distribution of less than about 1 μm.

The first dried molecular sieve catalyst composition is typically prepared by mixing the molecular sieve, the binder and the matrix materials in the presence of a liquid to form a slurry, and drying the slurry to form first dried molecular sieve catalyst particles.

The amount of binder used to prepare the first dried molecular sieve catalyst typically ranges from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the first dried molecular sieve catalyst composition is from 0:1 to 1:1, preferably 1:15 to 1:2, more preferably 1:10 to 1:2, and most preferably 1:6 to 1:1.

The liquid used to form the first dried molecular sieve catalyst can be any liquid known in the art of formulating catalysts. Non-limiting examples of suitable liquids include one or a combination of water, alcohol, ketones, aldehydes, and/or esters. The most preferred liquid is water.

The molecular sieve and matrix material, and the optional binder, used in making the first dried catalyst composition may be combined in the same or different liquid, and may be combined in any order, together, simultaneously, sequentially, or a combination thereof. In the preferred embodiment, the same liquid, preferably water, is used.

In one embodiment, the slurry of the molecular sieve, binder and matrix materials used to make the first dried catalyst composition is mixed or milled to achieve a uniform slurry of sub-particles of the molecular sieve catalyst composition; the slurry is then fed to a forming unit that produces the first dried molecular sieve catalyst composition. The forming unit may be any known unit, such as spray dryers, pelletizers, extruders, etc. In a preferred embodiment, the forming unit is spray dryer. Typically, the forming unit is maintained at a temperature sufficient to remove most of the liquid from the slurry.

When a spray dryer is used as the forming (or drying) unit, typically, the slurry of the molecular sieve and matrix material, and optionally a binder, is co-fed to the spray drying volume with a drying gas with an average inlet temperature ranging from 150° C. to 550° C., and a combined outlet temperature ranging from 100° C. to about 250° C.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kpaa to 6895 kpaa). In another embodiment, the slurry is co-fed through a single nozzle or multiple nozzles along with an atomisation fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a partially, substantially or totally dried molecular sieve catalyst composition.

An example of spray drying process that may be used to prepare the first dried molecular sieve catalyst composition is disclosed in U.S. Pat. No. 4,946,814, the description of which is incorporated herein.

In addition, the first dried molecular sieve catalyst composition used in the method of the present invention may comprise one or several other catalytically active materials, besides the molecular sieve(s). As a result, these other catalytically active materials are incorporated as a part of the first dried catalyst composition.

According to the present invention, the first dried molecular sieve catalyst is combined with water to form a water-catalyst composition, which is mixed to form a slurry. Preferably, the mixing is sufficient to break the larger particles added to the solution. In general, the more vigorous the mixing, the smaller the particles formed in the slurry. Mixing using high-shear mixers is preferred. In general, these are mixers which are capable of rotating at speeds of at least about 3,000 rpms laboratory scale equivalent.

The particle size of the slurry can be indirectly assessed by measuring the viscosity of the slurry. In general, the higher the viscosity, the smaller the particle size in the slurry. The viscosity of the slurry should not be too high so that mixing is not effective in breaking apart large particles or too low so that drying will not produce acceptable particle formation. In one embodiment of the invention, the slurry has a viscosity of from about 100 cP (0.1 Pa/sec) to about 9,500 cP (9.5 Pa/sec), as measured using a Brookfield LV-DVE viscometer with a No. 3 spindle at 10 rpm. Preferably the slurry has a viscosity of from about 200 cP (0.2 Pa/sec) to about 8,500 cP (8.5 Pa/sec), and more preferably from about 350 cP (0.375 Pa/sec) to about 8,000 cP (8 Pa/sec), as measured using a Brookfield LV-DVE viscometer with a No. 3 spindle at 10 rpm.

In another embodiment the slurry has a solids content of from about 10 wt % to about 75 wt %. Preferably the slurry has a solids content of from about 15 wt % to about 70 wt %, more preferably from about 20 wt % to about 65 wt %, based on the total weight of the slurry. The solids content can be measured using any conventional means. However, a CEM MAS 700 microwave muffle furnace is particularly preferred to give results consistent with the values recited herein.

If desired, the pH of the slurry can be adjusted before or during the mixing step.

The slurry can be dried using any conventional drying method to form a second dried molecular sieve catalyst composition. All the methods described earlier in this document to prepare the first dried molecular sieve catalyst composition are equally suitable to produce the second dried molecular sieve catalyst composition.

In one embodiment, the second dried molecular sieve catalyst composition is calcined. Calcination further hardens and/or activates the second dried molecular sieve catalyst composition. A conventional calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition are described in, for example, U.S. Pat. No. 5,185,310 (heating molecular sieve of gel alumina and water to 450 C.), PCT WO 00/75072 published Dec. 14, 2000 (heating to leave an amount of template), which are all herein fully incorporated by reference The process of the present invention provides methods to produce molecular sieve catalyst compositions containing particles with properties that make them suitable for catalytic use. They can be used, for example, to dry gases and liquids; for selective molecular separation based on size and polar properties; as an ion-exchanger; as a catalyst in hydrocarbon cracking, hydrocracking, disproportionation, alkylation, isomerization, oxidation, and conversion of oxygenates to hydrocarbons; as a chemical carrier; in gas chromatography; and in the petroleum industry to remove normal paraffins from distillates. The catalysts are particularly suited for use as catalysts in cracking, hydrocracking, disproportionation, alkylation, isomerization, oxidation, and conversion of oxygenates to hydrocarbons. More particularly, the molecular sieve catalysts of this invention are suited for use as a catalyst in the conversion of oxygenates to hydrocarbons.

In its most desired embodiment, the molecular sieve catalyst compositions made by the method of the invention can be used as a catalyst in the conversion of oxygenates to hydrocarbons. Hence, the present invention also encompasses a method for producing light olefins by contacting a feedstock comprising at least one oxygenate with a dried or calcined molecular sieve composition prepared by the method of the present invention.

In this embodiment, a feed containing an oxygenate is contacted in a reaction zone of a reactor apparatus with the molecular sieve catalyst composition at process conditions effective to produce light olefins, i.e., an effective temperature, pressure, WHSV (weight hour space velocity) and, optionally, an effective amount of diluent, correlated to produce light olefins. These conditions are described in detail below. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of between about 300° C. and 500° C. is desired.

The process can be carried out in a dynamic bed system or any system of a variety of transport beds rather than in a fixed bed system. It is particularly desirable to operate the reaction process at high space velocities and in a fluidized bed system.

The conversion of oxygenates to produce light olefins may be carried out in a variety of large scale catalytic reactors, including, but not limited to, fluid bed reactors and concurrent riser reactors as described in *Fluidization Engineering*, D. Kunii and O. Levenspiel, Robert E. Krieger Publishing Co. New York, 1977, incorporated in its entirety herein by reference. Additionally, countercurrent free fall reactors may be used in the conversion process. See, for example, U.S. Pat. No. 4,068,136 and *Fluidization and Fluid-Particle Systems*, pages 48–59, F. A. Zenz and D. F. Othmo, Reinhold Publishing Corp., New York, 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 $hr^{-1}$ to 1000 $hr^{-1}$. In the case of commercial scale reactors, WHSV is defined as the weight of hydrocarbon in the feed per hour per weight of molecular sieve content of the catalyst. The hydrocarbon content will be oxygenate and any hydrocarbon which may optionally be combined with the oxygenate. The molecular sieve content is intended to mean only the molecular sieve portion that is contained within the catalyst. This excludes components such as binders, diluents, inerts, rare earth components, etc.

The pressure also may vary over a wide range, including autogenous pressures. Desired pressures are in the range of about 0.5 kPa to about 5 MPa. The foregoing pressures refer to the partial pressure of the oxygenate compounds and/or mixtures thereof.

One or more inert diluents may be present in the feedstock, for example, in an amount of from 1 molar percent to 99 molar percent, based on the total number of moles of all feed and diluent components fed to the reaction zone (or catalyst). Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The desired diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a desired embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Desired oxygenate compounds are methanol, dimethyl ether, or a mixture thereof.

The method of making the desired olefin product in this invention can include the additional step of making these oxygenates from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

The olefins produced using the catalysts of this invention can be polymerized to form polyolefins, particularly polyethylene and polypropylene. Conventional processes for forming polyolefins from olefins can be used. Catalytic processes are desired. Particularly desired are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A desired polyolefin-forming catalyst is a metallocene catalyst. The desired temperature of operation is from 50° C. to 240° C. and the reaction can be carried out at low, medium or high pressure, being anywhere from about 1 bar to 200 bars. For processes carried out in solution, an inert diluent can be used, and the desired operating pressure is from 10 bars to 150 bars, with a desired temperature range of from 120° C. to 230° C. For gas phase processes, it is desired that the temperature generally from 60° C. to 160° C., and that the operating pressure from 5 bars to 50 bars.

In addition to polyolefins, numerous other olefin derivatives may be formed from the olefins produced by the catalysts of this invention. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

In the catalytic processes using the molecular sieve catalyst compositions produced according to the present invention, catalyst particles must meet certain particle requirements, including particle size, particle size distribution, particle density, and particle hardness. Examples of molecular sieve catalyst particle properties that have proved useful in catalytic processes include the following non-limiting examples.

After calcination, the particles of the second dried molecular sieve catalyst may have a particle size distribution such that not greater than about 10 wt % of the catalyst particles have an average diameter less than or equal to 20 $\mu$m; preferably not greater than about 5 wt % of the catalyst particles have an average diameter less than or equal to 20 $\mu$m, and more preferably not greater than about 2 wt % of the catalyst particles have an average diameter less than or equal to 20 $\mu$m. In another embodiment, the catalyst composition is comprised of catalyst particles, wherein, after calcination of the catalyst composition, not greater than about 10 wt % of the catalyst particles have an average diameter greater than or equal to about 250 $\mu$m; preferably not greater than about 5 wt % of the catalyst particles have an average diameter greater than or equal to about 250 $\mu$m, more preferably not greater than about 2 wt % of the catalyst particles have an average diameter greater than or equal to 250 $\mu$m.

In another embodiment of the invention, the calcined catalyst particles made according to the process of the invention have a particle distribution such that the catalyst composition is particularly suited for use in fluidized bed reaction systems. In one embodiment, the calcined catalyst has a particle distribution in $\mu$m of $2<d_{10}<50$; $30<d_{50}<120$; and $50<d_{90}<250$, wherein $d_{10}$ is the average diameter in which the cumulative volume of the sample reaches 10% of the total, $d_{50}$ is the average diameter in which the cumulative volume of the sample reaches 50% of the total, and $d_{90}$ is the average diameter in which the cumulative volume of the sample reaches 90% of the total. Preferably the calcined catalyst has a particle distribution in $\mu$m of $5<d_{10}<45$; $40<d_{50}<100$; and $70<d_{90}<200$, more preferably a particle distribution in $\mu$m of $10<d_{10}<40$; $50<d_{50}<100$; and $90<d_{90}<150$.

In another embodiment of this invention, the catalyst composition made from the method of this invention comprises particles which are highly attrition resistant. Such particles are particularly suited for use in fluidized catalytic systems.

In this invention, attrition resistance, or catalyst hardness, is measured using an ExxonMobil Attrition rate Index (EMARI). The EMARI is used over other measurement methods, since many other methods are not sufficient to measure very highly attrition resistant molecular sieve catalysts such as those made according to this invention.

The EMARI methodology is similar to the conventional Davison Index method. The smaller the EMARI, the more resistant to attrition, hence the harder, is the catalyst. The EMARI is measured by adding 6.0±0.1 g of catalyst having a particles size ranging from 53 to 125 microns to a hardened steel attrition cup. Approximately 23,700 scc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the EMARI, in wt %/hr.

$$EMARI=C/(B+C)/D \times 100\%$$

wherein

B=weight of catalyst left in the cup after the attrition test

C=weight of collected fine catalyst particles after the first hour of attrition treatment D=duration of treatment in hours after the first hour attrition treatment.

The calcined molecular sieve catalyst particles which are made from the method of this invention desirably have an EMARI of not greater than about 1 wt %/hr. Preferably the calcined molecular sieve catalyst particles have an EMARI of not greater than about 0.7 wt %/hr, more preferably not greater than about 0.3 wt %/hr.

The present invention thus also encompasses a calcined molecular sieve catalyst containing catalyst particles having an EMARI of not greater than about 1 wt %/hr, preferably of not greater than about 0.7 wt %/hr, more preferably of not greater than about 0.3 wt %/hr.

This invention will be better understood with reference to the following examples, which are intended to illustrate specific embodiments within the overall scope of the invention as claimed.

EXAMPLE 1

Dried molecular sieve catalyst compositions A1, A2, A3 (first dried molecular sieve catalyst compositions in the context of the present invention) were prepared according to the following procedure:

A slurry was made by mixing together water and a solid composition comprising 40 wt % SAPO-34, 10.6 wt % alumina derived from aluminum chlorohydrate (Reheis Chemicals Inc., Berkeley Heights, N.J.), and 49.4 wt % kaolin clay (Engelhard Corporation, Gordon, Ga.). The slurry was comprised of 45 wt % of the solid composition. The slurry was then dried in a spray dryer to yield first dried molecular sieve catalyst compositions A1, A2 and A3.

EXAMPLE 2

Slurries were made from each of the dried molecular sieve catalyst composition prepared in Example 1 by adding a portion of each of the first dried molecular sieve catalyst composition to deionized water to form a composition containing 45 wt % solids. The composition was initially stirred using a spatula. Then the composition was mixed using a Yamato DL-2100 mixer (Yamato Scientific America Inc., Orangeburg, N.Y.) at 600 rpm for 5 minutes, then at 2,400 rpm for 5 minutes.

The slurries obtained in this fashion from catalyst compositions A1, A2, A3 will be hereinafter referred to as Slurry 1, Slurry 2 and Slurry 3, respectively.

EXAMPLE 3

A portion of Slurry 1 and Slurry 2 obtained in Example 2 was further mixed using a Silverson SR4 high-shear mixer (Silverson Machines, Inc., Massachusetts) at 6,500 rpm for 3 minutes. The slurries obtained with high shear mixing will be hereinafter referred to as Slurry HS 1 and Slurry HS2, respectively.

EXAMPLE 4

Slurry 1 prepared at example 2 and Slurry HS1 prepared at example 3 were compared for viscosity. Each of the slurries were tested for viscosity using a Brookfield LV-DVE viscometer with a No. 3 spindle at various rpms. The results are shown in Table 1.

TABLE 1

| Slurry | Re-worked Slurry Viscosity | | | | |
| --- | --- | --- | --- | --- | --- |
| | Viscosity (cP) at Different rpms | | | | |
| | 100 rpm | 60 rpm | 30 rpm | 20 rpm | 10 rpm |
| Slurry 1 | 309 | 456 | 753 | 1044 | 1838 |
| Slurry HS1 | 338 | 510 | 880 | 1202 | 2112 |

The data in Table 1 indicate that the slurry made using high-shear mixing has a higher viscosity. This is an indication that the higher the viscosity the smaller the particle size of the solids in the slurry.

EXAMPLE 5

Portions of samples A1, A2 and A3 prepared in Example 1 were calcined in a muffle furnace at 650° C. in air for 2 hours. This yielded samples A1calc, A2calc and A3calc, respectively. The attrition resistance of these samples was determined using the EMARI test described in the specification. The results are shown in Table 2.

EXAMPLE 6

Portions of Slurry 2 and Slurry 3 prepared in Example 2 were spray dried using a Yamato DL-41 spray dryer, operating in a down spray mode using a 1 mm atomization nozzle. The spray drying conditions were: 40 g/min feed rate; 350° C. inlet temperature; 1 bar atomization pressure; 60% gas flow carrier setting. This yielded second dried molecular sieve compositions B2 and B3, respectively.

The spray dried products were collected in a cyclone, and calcined in a muffle furnace at 650° C. in air for 2 hours. This yielded samples B2calc and B3calc, respectively. The attrition resistance of these samples was determined using the EMARI test described in the specification. The results are shown in Table 2.

EXAMPLE 7

Portions of Slurry HS1 and Slurry HS2 prepared at example 3 were spray dried using a Yamato DL-41 spray dryer, operating in a down spray mode using a 1 mm atomization nozzle. The spray drying conditions were: 40 g/min feed rate; 350° C. inlet temperature; 1 bar atomization pressure; 60% gas flow carrier setting. This yielded second dried molecular sieve samples C1 and C2, respectively. The spray dried products were collected in a cyclone, and calcined in a muffle furnace at 650° C. in air for 2 hours. This yielded samples C1calc and C2calc, respectively. The attrition resistance of these samples was determined using the EMARI test described in the specification. The results are shown in Table 2.

TABLE 2

EMARI (wt %/hr) of calcined molecular sieve catalysts.

| Example 5 | | Example 6 | | Example 7 | |
|---|---|---|---|---|---|
| Sample | EMARI | Sample | EMARI | Sample | EMARI |
| A1 calc | 1.48 | — | — | C1calc | 0.25 |
| A2 calc | 1.37 | B2calc | 0.83 | C2calc | 0.21 |
| A3 calc | 0.85 | B3calc | 0.63 | — | — |

The lower the EMARI, the harder the material, or the greater the attrition resistance.

EXAMPLE 8

Samples B2calc, B3calc, C1calc and C2calc prepared in Examples 6 and 7 were analyzed for particle size distribution using a Microtrac S3000 laser scattering particle size analyzer (Microtrac Inc., Clearwater, Fla.). The data are shown in Table 3.

TABLE 3

Particle size distribution in calcined molecular sieve catalysts.

| | Particle Size | | | | | | | | | |
|---|---|---|---|---|---|---|---|---|---|---|
| S. No. | $d_{10}$ | $d_{20}$ | $d_{30}$ | $d_{40}$ | $d_{50}$ | $d_{60}$ | $d_{70}$ | $d_{80}$ | $d_{90}$ | $d_{95}$ |
| B2calc | 14.4 | 20.9 | 27.0 | 33.0 | 39.1 | 45.8 | 54.6 | 70.1 | 120.2 | 185.5 |
| B3calc | 14.4 | 21.4 | 28.1 | 34.8 | 42.0 | 51.2 | 67.0 | 112.2 | 188.5 | 240.8 |
| C1calc | 14.1 | 20.0 | 25.0 | 29.9 | 35.2 | 41.5 | 49.2 | 58.9 | 72.0 | 82.4 |
| C2calc | 12.9 | 18.5 | 23.8 | 29.2 | 34.7 | 40.5 | 47.2 | 56.2 | 73.3 | 95.8 |

All of the samples shown in Table 3 are considered to be calcined material made from the method of this invention. The data in Table 3 show that the material made from the high-shear mixed slurry (C1calc and C2calc) had fewer large particles after calcination than samples B2calc and B3calc.

Having now fully described this invention, it will be appreciated by those skilled in the art that the invention can be performed within a wide range of parameters within what is claimed, without departing from the spirit and scope of the invention.

What is claimed is:

1. A method of making molecular sieve catalyst particles, comprising
   a) providing a first dried molecular sieve catalyst made of catalyst particles that contain molecular sieve particles bound together to form catalyst particles larger than the individual molecular sieve particles;
   b) combining the first dried molecular sieve catalyst with water to form a water-catalyst composition;
   c) mixing the water-catalyst composition to form a slurry; and
   d) drying the slurry to form particles of a second dried molecular sieve catalyst.
2. The method of claim 1, wherein the water used in b) comprises at least 95 wt % water.
3. The method of claim 1, wherein the water used in b) is substantially free of any molecular sieve particle.
4. The method of claim 1, wherein the first dried molecular sieve catalyst contains template material.
5. The method of claim 4, wherein the template is selected from the group consisting of triethylanilne, cyclohexylanilne, piperidine, dipropylamine, pyridine, isopropylainine, tetraethyl ammonium salts, and mixtures thereof.
6. The method of claim 1, wherein the water-catalyst composition is mixed so that the slurry obtained in c) contains particles smaller than the particles contained in the first dried molecular sieve catalyst.
7. The method of claim 1, further comprising e) calcining the particles of said second dried molecular sieve catalyst.
8. The method of claim 1, wherein the particle size of the first dried molecular sieve catalyst is such that, after calcination, 10 wt % of the particles have an average particle diameter less than or equal to 20 µm.
9. The method of claim 1, wherein the water is at a substantially neutral pH prior to combining with the first dried molecular sieve catalyst.
10. The method of claim 1, wherein the slurry has a viscosity of from 100 cP to 9,000 cP measured using a Brookfield LV-DVE viscometer with a No. 3 spindle at 10 rpm.
11. The method of claim 1, wherein the slurry prepared in c) has a solids content of from 10 wt % to 75 wt %.
12. The method of claim 7, wherein the molecular sieve catalyst particles obtained in e) have an EMARI of not greater than 1 wt %/hr.
13. The method of claim 7, wherein the molecular sieve catalyst particles obtained in e) have a particle size such that 50% of the particles have a diameter larger than 30 µm and smaller than 150 µm.
14. The method of claim 1, wherein drying the slurry in d) is by spray drying.
15. The method of claim 1, wherein the first dried molecular sieve catalyst comprises a silicoaluminophosphate molecular sieve.
16. The method of claim 15, wherein the silicoaluminophosphate molecular sieve is selected from the group consisting of SAPO-18, SAPO-34, SAPO-35, SAPO-44, SAPO-56, ALPO-18 and ALPO-34, metal containing molecular sieves thereof, and mixtures thereof.
17. The method of claim 16, wherein silicoaluminophosphate molecular sieve is selected from the group consisting of SAPO-18, SAPO-34, ALPO-34 and ALPO-18, metal containing molecular sieves thereof, and mixtures thereof.
18. The method of claim 17, wherein the silicoaluminophosphate molecular sieve has a framework-type selected from the group consisting of CHA, AEI and a combination thereof.
19. The method of claim 1, wherein the first dried molecular sieve catalyst comprises an inorgarnic oxide sol binder.
20. The method of claim 19, wherein the binder is aluminium chlorohydrate.
21. The method of claim 1, wherein the first dried molecular sieve catalyst comprises a clay filler.
22. A method of recycling molecular sieve catalyst particles having undesired properties, comprising
   (a) mixing a composition comprising molecular sieve, binder and water;
   (b) drying the composition to form a first dried molecular sieve catalyst made of molecular sieve particles bound together to form particles larger than the individual molecular sieve particles;

(c) combining at least a portion of the first dried molecular sieve catalyst with water to form a water-catalyst composition;

(d) mixing the water-catalyst composition to form a slurry;

(e) drying the slurry to form particles of a second dried molecular sieve catalyst.

23. The method of claim 22, further comprising (f) calcining the particles of said second dried molecular sieve catalyst.

24. The method of claim 23, wherein the calcined catalyst particles have an EMARI of not greater than 1 wt %/hr.

25. The method of claim 23, wherein the calcined catalyst particles have a particle size such that 50% of the particles have a diameter larger than 30 μm and smaller than 150 μm.

26. The method of claim 22, wherein drying the slurry in b is by spray drying.

27. The method of claim 22, wherein the first dried molecular sieve catalyst comprises a silicoaluminophosphate molecular sieve.

28. The method of claim 27, wherein the silicoaluminophosphate molecular sieve is selected from the group consisting of SAPO-18, SAPO-34, SAPO-35, SAPO-44, SAPO-56, ALPO-18 and ALPO-34, metal containing molecular sieves thereof, and mixtures thereof.

29. The method of claim 27, wherein silicoaluminophosphate molecular sieve is selected from the group consisting of SAPO-18, SAPO-34, ALPO-34 and ALPO-18, metal containing molecular sieves thereof, and mixtures thereof.

30. The method of claim 27, wherein the silicoaluminophosphate molecular sieve has a framework-type selected from the group consisting of CHA, AEI and a combination thereof.

31. The method of claim 22, wherein the first dried molecular sieve catalyst comprises an inorganic oxide sol binder.

32. The method of claim 31, wherein the binder is aluminum chlorohydrate.

33. The method of claim 22, wherein the first dried molecular sieve catalyst comprises a clay filler.

34. A method of making a molecular sieve catalyst composition comprising;

providing first dried molecular sieve catalyst particles made of molecular sieve particles bound together to form particles larger than the individual molecular sieve particles, wherein the first dried molecular sieve catalyst particles yield, upon calcining, a calcined molecular sieve composition having greater than 5 wt % catalyst particles having an average particle diameter greater than or equal to 250 microns;

combining the dried molecular sieve catalyst particles with water to form a slurry; and drying the slurry to form the molecular sieve catalyst composition.

35. The method of claim 34, wherein the provided first dried molecular sieve catalyst particles contain template material.

36. The method of claim 34, wherein the provided first dried molecular sieve catalyst particles are mixed with the water so that at least a portion of the first dried molecular sieve catalyst particles break apart.

37. The method of claim 34, wherein the provided first dried molecular sieve catalyst particles yield, upon calcining, a calcined molecular sieve composition having greater than 10 wt % catalyst particles having an average particle diameter less than or equal to 10 microns.

38. The method of claim 34, further comprising combining the provided first dried molecular sieve catalyst particles with water prior to mixing, wherein the water is at a substantially neutral pH prior to adding the particles.

39. The method of claim 34, wherein the slurry has a viscosity of from 100 cP to 9,000 cP measured using a Brookfield LV-DVE viscometer with a No. 3 spindle at 10 rpm.

40. The method of claim 34, wherein the slurry has a solids content of from 10 wt % to 75 wt %.

41. The method of claim 34, further comprising calcining the molecular sieve catalyst composition formed from drying the slurry.

42. The method of claim 41, wherein the calcined molecular sieve catalyst particles have an EMARI of not greater than 1 wt %/hr.

43. The method of claim 41, wherein the calcined molecular sieve catalyst particles have a particle size such that 50% of the particles have a diameter larger than 30 μm and smaller than 50 μm.

44. The method of claim 34, wherein drying the slurry is by spray drying.

45. The method of claim 34, wherein the provided first dried molecular sieve catalyst particles comprise silicoaluminophosphate molecular sieve.

46. The method of claim 45, wherein the silicoaluminophosphate molecular sieve is selected from the group consisting of SAPO-18, SAPO-34, SAPO-35, SAPO-44, SAPO-56, ALPO-18 and ALPO-34, metal containing molecular sieves thereof, and mixtures thereof.

47. The method of claim 45, wherein silicoaluminophosphate molecular sieve is selected from the group consisting of SAPO-18, SAPO-34, ALPO-34 and ALPO-18, metal containing molecular sieves thereof, and mixtures thereof.

48. The method of claim 45, wherein the silicoaluminphosphate molecular sieve has a framework-type selected from the group consisting of CHA, AEI and a combination thereof.

49. The method of claim 34, wherein the provided first dried molecular sieve catalyst particles comprises an inorganic oxide sol binder.

50. The method of claim 49, wherein the binder is aluminium chlorohydrate.

51. The method of claim 50, wherein the provided first dried molecular sieve catalyst comprises a clay filler.

52. A calcined molecular sieve catalyst composition comprising catalyst particles that contain molecular sieve particles bound together to form catalyst particles larger than the individual molecular sieve particles, wherein the catalyst particles, after being submitted to calcination, have an EMARI of equal or less than 0.7 wt %/hr.

53. The method of claim 1, wherein the step of providing a first dried molecular sieve catalyst comprises:

(i) mixing a composition comprising molecular sieve, binder and water; and (ii) drying the composition to form the first dried molecular sieve catalyst.

54. The method of claim 2, wherein the water used in b) comprises at least 97 wt % water.

55. The method of claim 54, wherein the water used in b) comprises at least 98 wt % water.

56. The method of claim 12, wherein the molecular sieve catalyst particles obtained in e) have an EMARI of not greater than 0.7 wt %/hr.

57. The method of claim 56, wherein the molecular sieve catalyst particles obtained in e) have an EMARI of not greater than 0.3 wt %/hr.

58. The method of claim 24, wherein the molecular sieve catalyst particles obtained in e) have an EMARI of not greater than 0.7 wt %/hr.

59. The method of claim 58, wherein the molecular sieve catalyst particles obtained in e) have an EMARI of not greater than 0.3 wt %/hr.

60. The method of claim 42, wherein the molecular sieve catalyst particles obtained in e) have an EMARI of not greater than 0.7 wt %/hr.

61. The method of claim 60, wherein the molecular sieve catalyst particles obtained in e) have an EMARI of not greater than 0.3 wt %/hr.

62. The calcined molecular sieve catalyst composition of claim 52, wherein the catalyst particles, after being submitted to calcination, have an EMARI of equal or less than 0.3 wt %/hr.

* * * * *